United States Patent [19]

Palmberg

[11] Patent Number: 4,638,446

[45] Date of Patent: Jan. 20, 1987

[54] APPARATUS AND METHOD FOR REDUCING TOPOGRAPHICAL EFFECTS IN AN AUGER IMAGE

[75] Inventor: Paul W. Palmberg, Bloomington, Minn.

[73] Assignee: The Perkin-Elmer Corporation, Norwalk, Conn.

[21] Appl. No.: 499,596

[22] Filed: May 31, 1983

[51] Int. Cl.$^4$ .............................................. H01J 39/00
[52] U.S. Cl. .................................... 364/555; 250/305; 364/498
[58] Field of Search .................. 364/498, 555; 377/10, 377/11, 44; 250/305

[56] References Cited

U.S. PATENT DOCUMENTS

| | | | |
|---|---|---|---|
| 3,914,606 | 10/1975 | Hashimoto et al. | 250/305 |
| 3,938,038 | 2/1976 | Campbell | 364/555 X |
| 4,001,699 | 1/1977 | Denny et al. | 377/39 X |
| 4,165,459 | 8/1979 | Curtice | 377/44 X |
| 4,179,604 | 12/1979 | Christon | 250/305 X |
| 4,255,809 | 3/1981 | Hillman | 377/39 X |
| 4,382,181 | 5/1983 | Wang | 250/305 |
| 4,459,482 | 7/1984 | Bales | 250/305 |
| 4,491,926 | 1/1985 | Okada et al. | 377/11 X |

OTHER PUBLICATIONS

Janssen et al., "A Ratio Technique for Micro-Auger Analysis", *Surface Science*, 62 (1977) pp. 277-291.
Browning et al, "A Digital Scanning Auger Electron Microscope", *Surface Science*, 68 (Nov. 1977) pp. 328-337.

*Primary Examiner*—Parshotam S. Lall
*Assistant Examiner*—H. R. Herndon
*Attorney, Agent, or Firm*—Edwin T. Grimes; Francis L. Masselle; Thomas P. Murphy

[57] ABSTRACT

A system for producing an Auger image which is substantially independent of the topographical contour of the sample surface includes at least two counting means. Preferably, the two counting means are adapted to be dedicated counters, one for background incidents and one for signal incidents. The system also includes counter control means for regulating the counting time and the immersion incident energy threshold for each counter.

6 Claims, 1 Drawing Figure

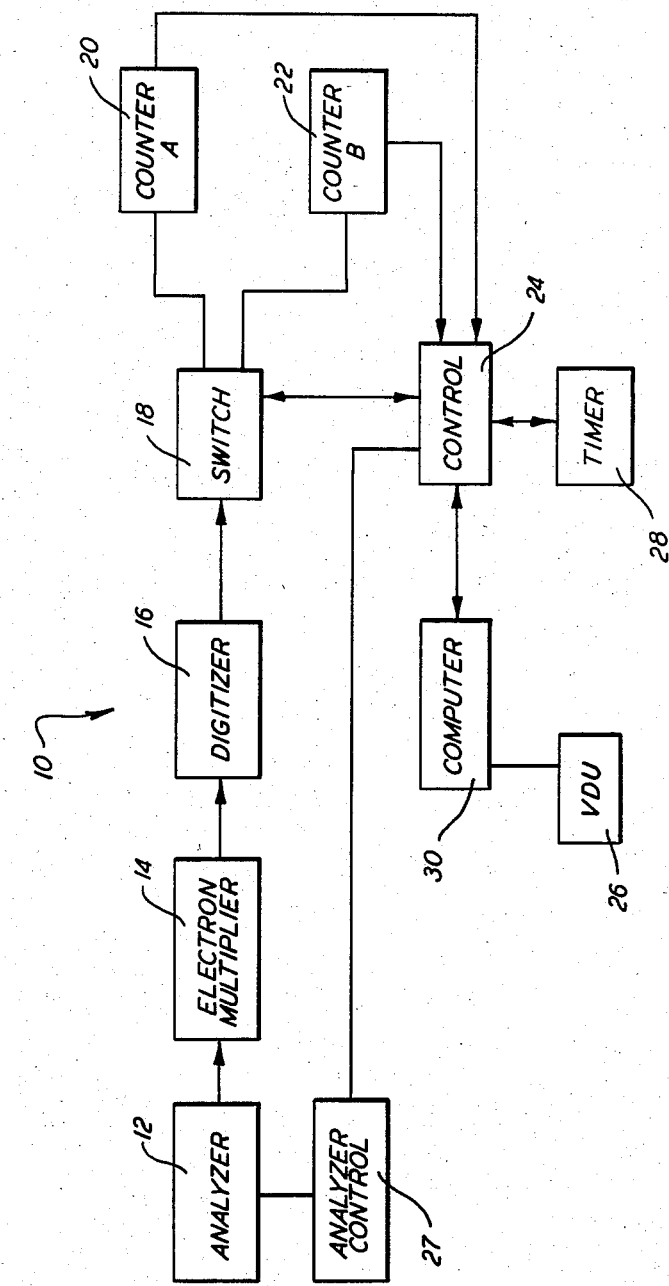

APPARATUS AND METHOD FOR REDUCING TOPOGRAPHICAL EFFECTS IN AN AUGER IMAGE

BACKGROUND OF THE INVENTION

The present invention generally relates to an apparatus for producing an Auger image and, in particular, relates to such an apparatus which is substantially independent of the topographical contour of the sample under test.

Auger analysis in a sophisticated analytical technique whereby the surface of a sample is examined for its elemental composition. When discussing Auger systems, the term "surface" is generally considered to be that portion of the sample which is on the order of a few atomic layers deep. During an Auger analysis, a primary electron source bombards a segment of the sample surface to release secondary electrons (i.e. Auger electrons) therefrom, which secondary electrons are collected and analyzed. The liberated particles are usually analyzed as a function of their energy.

As well known in the art, one particularly convenient means for evaluating the data generated by an Auger system is to create an Auger image, or map. To create such a map, the technologist generally measures the intensity of an Auger peak for a two-dimensional array of points on the sample being tested. In such an analysis, the primary electron beam is digitally controlled by a computer and stepped through a rectangular area of the sample surface. The points on the map are usually scanned in a raster pattern simlilar to that used for producing a television image. To form such an Auger image of a surface, the magnitude of the Auger peaks are first measured at each point in the raster matrix. This information is generally stored in a memory device and later displayed on, for example, an oscilloscope or other form of recorder where the intensity at each point of the raster is proportional to the magnitude of the Auger peak.

The intensity of a particular Auger peak is generally obtained by measuring the magnitude, $N(e_p)$ of the peak at the energy, $e_p$, giving maximum intensity and subtracting the background magnitude $N(e_b)$ at an energy $e_b$ sufficiently removed from the peak that Auger electrons forming the peak do not contribute. In conventional computer-controlled Auger systems, Auger maps are determined by the following steps: First, an electron-pass energy, $e_p$, is selected. After the pass energy is determined and the mechanism set, the number of incidences $N(e_p)$ is measured and stored for each point in a selected line of the raster matrix. Thereafter, the pass energy for the detector is set at another base line, $e_b$, representative of the electron energy of the background which is present. Thereafter, the incidences of background $N(e_b)$ is measured for each point in the same matrix. These measurements $N(e_p)$ and $N(e_b)$, taken at $e_p$ and $e_b$, respectively, are repeated for each line in the matrix. From the accumulated data an Auger image is constructed by conventional arithmetic processing equipment by subtracting the number of counts at $e_b$ from the number of counts $e_p$ at each point in the matrix.

A first order topographical correction can be achieved by dividing the peak height determined from above by the background incidences, i.e., $[N(e_p) - N(e_b)]/N(e_b)$. This is a fairly accurate correction to the topographical variations which modulate the background and peak height uniformly. This particular method is advantageous in that it is independent of the incident beam current since both the background and the peak are proportional to the excitation beam. Therefore, beam current variations having a period longer than the time required to scan each line do not affect the normalized Auger intensities.

Unfortunately, the above normalization scheme only removes beam current noise of rather low frequency. For example, if a particular line of the matrix contains 200 measurement points with a typical measurement time at each point of ten milliseconds, the elapsed time between the peak and the background measurements is therefore two seconds. Hence the technique is only effective in removing noise components having a frequency less than 0.5 Hz.

Another disadvantage is that by the use of equal measurement intervals at each spatial point, non-uniform statistical noise levels are created when topographical effects, i.e., surface depth variations, vary the signal magnitude either through scattering, absorption or miscellaneous reflections. Hence, even using a first order topographical correction, the variation of the Auger peak due to actual compositional changes of the surface is difficult to distinguish from changes due to noise variations along each particular line, as well as between different lines. As a result, topological variations can result in a complete mischaracterization of the elemental composition of a surface.

SUMMARY OF THE INVENTION

Accordingly, it is one object of the present invention to provide an apparatus for yielding a uniform background noise level in an Auger image and to prevent low frequency noise in the beam current on other instrumental factors from affecting the Auger image.

This object is achieved, at least in part, by measuring the background and the signal of interest in rapid succession at each point and by varying the measurement time per point to achieve a uniform noise level due to statistical noise in the background.

Other objects and advantages will become apparent to those skilled in the art from the following detailed specification, the accompanying drawing and the claims appended hereto.

BRIEF DESCRIPTION OF THE DRAWING

The single FIGURE of the drawing, not drawn to scale, is a block diagram of an apparatus, embodying the principles of the present invention, for reducing topographical effects in an Auger image.

DETAILED DESCRIPTION OF THE INVENTION

A system, generally indicated at 10 in the drawing and embodying the principles of the present invention, for reducing topographical effects in forming an Auger image includes a conventional Auger analyzer 12 for detecting secondary, or Auger, electrons. The system 10 also includes means 14 for amplifying the detected signal, the means 14 is preferably a conventional electron multiplier well known in the art. The signal from the multiplier 14 is digitized by a conventional V/F digitizer 16 which transforms the signals from the electron multiplier 14 into digital pulses. The signal from the digitizer 16 is then provided via a switch means 18 to first and second counters 20 and 22, respectively. The counters, 20 and 22, can be of any type known in the art;

for example, they can be semiconductor chips such as TI 74LS191 manufactured and marketed by Texas Instruments Corp. The switch means 18 is preferably a logical AND gate, such as an 74LS08-TI also manufactured and marketed by Texas Instruments Corp. The outputs from the counters, 20 and 22, are directed into a statistical processing control unit 24 the output of which is provided to a recorder and/or display mechanism 26 which can be, for example, a video display unit.

In one mode of operation, the primary electron source bombards one point of the surface under test to liberate secondary electrons therefrom. The pass energy for the analyzer 12 is set at $e_b$ by the control 24, one output of which is coupled to the analyzer 12 via an analyzer control unit 27. The digitized signals are counted, via the electron multiplier 14 and signal digitizer 16, into the first counter 20. A timer 28 is simultaneously activated and used to measure the time, $\Delta T$, required to bring the signal level in the first counter 20 to a preset value. The pass energy of the analyzer 12 is then set at $e_p$ and the second counter 22 is used to measure the signal level during the same time interval, $\Delta T$. Thus, the number of incidences of signals at energy level $e_b$ is initially accumulated by the first counter 20 until a particular preselected value has been reached. Then, the number of incidences of particles at energy $e_p$ is counted for the same point on the surface and for the same period of time. This value is recorded in second counter 22. As a result, the normalized Auger signal is the direct difference, which can be determined by, for example, a computer means 30, between this measured $N(e_p)$ signal and the preselected level $N(e_b)$. This signal is then provided to the display mechanism 26. Thus, the difference is provided on the screen of an oscilloscope as, for example, a function of the intensity. After both of these measurements have taken place, the primary electron source, not shown, is focused on the next adjacent point in the particular line of a raster pattern and the process repeated. This particular embodiment greatly reduces instrument or beam current errors by reducing the time interval between the $e_p$ and the $e_b$ measurement. For example, for a $\Delta T$ measurement time of 10 milliseconds per point, noise components having frequencies less than 100 Hz are rejected. In addition, by varying the $\Delta T$ per point along each line to establish a constant background signal, the statistical uncertainty, i.e., the shot noise level, is identical for each point in the raster scan.

Utilizing the same components, an Auger image can be produced which may, in fact, provide a larger signal-to-noise ratio capability. In this alternative embodiment, the first counter 20 is arranged, via the computer 30 and the control unit 24, to count the number of incidences of the background signal whereas the second counter 22 is arranged to count only those instances at the peak Auger energy, $e_p$. During a preselected particular time interval, the signal from the signal digitizer 16 is switched, via switch means 18, at a high frequency between the first and second counters 20 and 22, respectively. Simultaneously, the pass energy of the analyzer 12 is switched, via the control unit 24, between $e_b$ and $e_p$. In this manner, a signal proportional to the two signal levels, $e_b$ and $e_p$, is simultaneously accumulated in the counters 20 and 22. In this embodiment, the measurement at each point of the matrix is terminated when the background count, for example, in counter 20 reaches a predetermined level. In this fashion, the normalized Auger signal is then the difference between the value in the second counter 22 and the predetermined background level.

One important aspect in implementing this alternative embodiment is to ensure that the switching time between the counters, 20 and 22, is small compared with the time required for the number of background counts to achieve its predetermined level. As a result, by reducing the switching time, the frequency of the noise rejection is extended upwardly.

The embodiments described herein are particularly advantageous for use with primary electron guns which are conventionally characterized as having low frequency flicker noise in addition to inherent white or shot noise.

While the above embodiments are specifically described, they are intended to be exemplary of the present invention and other variations may be recognized by those skilled in the art, without departing from the true scope and spirit of the present invention. As such, the scope and spirit of this invention is deemed limited only by the claims appended hereto and the reasonable interpretation thereof.

What is claimed is:

1. A system for reducing topographical effects in forming an Auger image by sequentially focusing a primary electron source at points along a line of a raster pattern, said system comprising:

an electron analyzer, said analyzer having means for selectively passing electrons therethrough at a first preselected energy level and at a second preselected energy level, said analyzer producing a signal responsive to the passage therethrough of said electrons;

means for digitizing said signal from said analyzer;

first and second digital counters, each said counter being switchably connected to said digitizing means;

a timer;

control means having first means for connecting said first counter to said digitizing means and for setting said electron analyzer at said first energy level and for activating said timer to determine the time interval to bring the signal in the first counter to a preselected value, and said control means having second means for connecting said second counter to said digitizing means and for setting said electron analyzer at said second energy level to ascertain the signal in the second counter after the lapse of the same time interval;

means for calculating the difference between the count in said first counter and the count in said second counter;

means for displaying said difference in said counters; and means for refocusing said primary electron source on the next adjacent point along said line of the raster pattern.

2. System as claimed in claim 1 wherein:

said controlling means includes a dedicated computer which interfaces with said display means.

3. A method for reducing topographical effects in forming an Auger image by sequentially focusing a primary electron source at points along a line of a raster pattern, said method comprises the steps of:

digitizing the signal from an electron analyzer;

counting a preselected number of digitized signals while said analyzer passes electrons having less than a first preselected energy;

measuring the time interval required to count said preselected number of digitized signals;

counting, for an equivalent time interval, the number of digitized signals which said analyzer passes having less than a second preselected energy, said second preselected pass energy being greater than said fist preselected pass energy; and determining the difference between said preselected number of counts and said number of counts of said digitized signals having less than said second preselected pass energy; and refocusing said primary electron source on the next adjacent point along said line of said raster pattern and repeating said foregoing steps.

4. Method as claimed in claim 3 further comprising:
displaying said determined difference on a video display unit as a function of the intensity thereon.

5. A system for reducing topographical effects in forming an Auger image by sequentially focusing a primary electron source at points along a line of a raster pattern, said system comprising:

an electron analyzer, said analyzer having means for selectively passing electrons therethrough at a first preselected energy level and at a second preselected energy level, said analyzer producing a signal responsive to the passage therethrough of said electrons;

means for digitizing said signals from said analyzer;

first and second digital counters, each said counter being switchably connected to said digitizing means;

control means having first means for connecting said first counter to said digitizing means and for setting said electron analyzer at said first energy level when operating in a first mode, and said control means having second means for connecting said second counter to said digitizing means and for setting said electron analyzer at said second energy level when operating in a second mode, said control means having third means for switching said control means between said first and second modes a plurality of times until said first counter reaches a preselected value; means for ascertaining the count in said second counter when said first counter reaches said preselected value;

means for calculating the difference between the count in said first counter and the count in said second counter;

means for displaying said difference in said counters; and means for refocusing said primary electron source on the next adjacent point along said line of the raster pattern.

6. A method for reducing topographical effects in forming an Auger image by sequentially focusing a primary electron source at points along a line of a raster pattern, said method comprises the steps of:

digitizing the signal from an electron analyzer using digitizing means;

connecting a first counter to said digitizing means and setting said electron analyzer at a first energy level when operating in a first mode, and connecting a second counter to said digitizing means and setting said electron analyzer at a second energy level when operating in a second mode;

switching between said first and second modes a plurality of times until said first counter reaches a preselected value;

ascertaining the count in said second counter when said first counter reaches said preselected value;

calculating the difference between the count in said first counter and the count in said second counter;

displaying said difference in counts; and refocusing said primary electron source on the next adjacent point along said line of the raster pattern and repeating said foregoing steps.

* * * * *